(12) United States Patent
Inukai et al.

(10) Patent No.: US 7,232,428 B1
(45) Date of Patent: Jun. 19, 2007

(54) MEDICAL COCK

(75) Inventors: Kazuaki Inukai, Tokyo (JP); Susumu Miyasaka, Tokyo (JP); Kazuhiro Abe, Tokyo (JP); Hideyuki Makino, Tokyo (JP)

(73) Assignee: Nippon Sherwood Medical Industries, Ltd., Tokyo (JP)

( * ) Notice: Subject to any disclaimer, the term of this patent is extended or adjusted under 35 U.S.C. 154(b) by 0 days.

(21) Appl. No.: 10/148,360

(22) PCT Filed: Nov. 29, 1999

(86) PCT No.: PCT/JP99/06633

§ 371 (c)(1),
(2), (4) Date: May 25, 2002

(87) PCT Pub. No.: WO01/39826

PCT Pub. Date: Jun. 7, 2001

(51) Int. Cl.
*A61M 5/00* (2006.01)
(52) U.S. Cl. .................................................. 604/248
(58) Field of Classification Search ................ 604/248, 604/246, 247, 256, 167.01, 167.05, 167.03, 604/284; 128/912; 137/625.4, 625.46, 625.47, 137/625.41
See application file for complete search history.

(56) References Cited

U.S. PATENT DOCUMENTS

| 1,493,133 | A |   | 5/1924 | Sykora |
| 3,807,691 | A |   | 4/1974 | Barley |
| 3,957,082 | A | * | 5/1976 | Fuson et al. ........... 137/625.41 |
| 4,436,116 | A | * | 3/1984 | Billeter .................. 137/625.47 |
| 4,865,583 | A | * | 9/1989 | Tu .............................. 604/508 |
| 5,122,123 | A | * | 6/1992 | Vaillancourt ................ 604/192 |
| 5,144,972 | A |   | 9/1992 | Dryden |
| 5,968,011 | A | * | 10/1999 | Larsen et al. .......... 604/288.02 |

FOREIGN PATENT DOCUMENTS

DE    30 19 426 A1    11/1981

\* cited by examiner

*Primary Examiner*—Nicholas Lucchesi
*Assistant Examiner*—Theodore J. Stigell
(74) *Attorney, Agent, or Firm*—Muramatsu & Associates

(57) ABSTRACT

A sealable access stopcock includes a valve body having a switching part formed in a valve shaft thereof for switching from one flow passage to another; and a main body having an internal chamber in which the valve shaft of the valve body is rotatably fitted, and a plurality of tributary tubes each having a lumen extending therethrough, the lumen opening on a side wall of the internal chamber; the valve body being rotated to selectively bring the lumens into communication with one another through the switching part and thereby switch flow of an infusion fluid from one flow passage to another. A switching channel is provided in the form of an arcuate groove in the switching part of the valve shaft to extend along the circumferential surface thereof.

5 Claims, 13 Drawing Sheets

(a)

(b)

(a)

(b)

(a)

(b)

(a)

(b)

(a)

(b)

MEDICAL COCK

TECHNICAL FIELD

The present invention relates to a sealable access stopcock. More particularly, the present invention relates to a sealable access stopcock including a plurality of tributary tubes for connecting an infusion tube and a switching part for switching from one flow passage to another. Such a stopcock is provided on a flow passage of infusion fluid to allow mixed infusion of an additional drug solution by switching the flow passage, or a syringe may be connected to the tributary tube through its needle to inject another drug solution or to collect a blood sample by switching from one tributary tube to another as desired.

BACKGROUND ART 3-way stopcocks are known as one type of such medical instruments. A 3-way stopcock includes three tributary tubes that are separated from one another by an angle of, for example, 90°. FIGS. 11(a) and 11(b) shows construction of the conventional 3-way stopcock while FIGS. 12(a)–12(b) and 13(a)–13(b) each illustrates one application of the conventional 3-way stopcock, with (a) in each figure being a plan view and (b) being a cross-section. FIG. 14 shows one application of a construction shown in FIGS. 13(a) and 13(b).

In FIGS. 11(a) and 11(b), a reference numeral 1 denotes a 3-way stopcock, a reference numeral 2 denotes a main body thereof, and reference numerals 5, 6, and 7 each indicates a tributary tube. The tributary tubes 5, 6, and 7 are separated from one another by 90°. A reference numeral 8 denotes a thread formed at an end of each of the tributary tubes 5 and 7 whereas a reference numeral 9 denotes a tapered portion formed on one end of the tributary tube 6. A cap is normally placed over each of the threads 8.

Reference numerals 12, 13, and 14 indicate a valve body, a valve shaft, and a handle, respectively. A reference numeral 16 denotes a T-shaped switching conduit formed through the valve shaft 13. The valve shaft 13 of the valve body 12 is fitted into the main body 2. The flow of infusion fluid is switched from one flow passage to another by turning the valve body 12 through the handle 14 so that the switching conduit 16 communicates with the tributary tubes 5, 6, and 7 in turn. An infusion tube, connected to a source of infusion fluid, is connected to the tributary tube 5 through the thread 8 while another tube, connected to a blood vessel, is connected to the tapered portion 9 of the tributary tube 6.

Referring to FIGS. 12 through 14, reference numerals 10, 20, 22, 23, and 50 denote a septum, a cylinder of a syringe (injection cylinder), a connector, a blunt needle, and a plug (infusion plug), respectively. The plug 50 is connected to the tributary tube 7 through the thread 8. Referring to FIGS. 13(a) and 13(b), a 3-way stopcock 1 includes a septum 10 similar to the one shown in FIGS. 12(a) and 12(b). The septum 10 is placed in a relatively short tributary tube 7. Structure of the connector 22 including the blunt needle 23 will be described later. In FIGS. 12(b) and 13(b), a reference numeral 40 indicates air bubbles. The area containing the air bubbles represents an internal space of the tributary tube 7 (i.e., dead space).

The conventional 3-way stopcock 1 as shown in FIG. 11 is arranged between a patient and a source of infusion fluid so that when the valve body 12 is turned, the flow of infusion fluid is selectively switched from one flow passage to another. However, while the tributary tubes 5 and 6 are in communication with each other for administration of a drug solution, the tributary tube 7, not in use, is left unattended without any sanitary measure being taken except for the above-mentioned cap placed over the thread 8. Accordingly, there is a risk of microbial contamination from the end region of the tributary tube 7. Also, there is a concern that the drug solution remaining within the tributary tube 7, which radially extends away from the main body 2, provides an ideal breeding ground for bacteria.

Among various drug solutions, intravenous hyperalimentation may provide an optimum growth medium for bacteria. In particular, the end region of the syringe 20 is subjected to the possibility of contamination through contact with the surrounding atmosphere or linens each time the syringe 20 is attached to, or removed from, the tributary tube 7 of the 3-way stopcock 1. In addition, the deep hollow construction of the tributary tube 7 makes it difficult to wipe off the remaining solution and sterilize the tube, which often results in insufficient sanitary procedures. For this reason, once bacteria enter the tributary tube 7, it is extremely difficult to prevent their growth.

An approach devised by medical practitioners in an effort to cope with these problems involves use of the 3-way stopcock 1 in conjunction with the plug 50 as shown in FIGS. 12(a) and 12(b). Each of the constructions shown in FIGS. 12(a) and 12(b) and in FIGS. 13(a) and 13(b) includes the septum 10 on one end of the tributary tube 7 for isolation from the surrounding atmosphere and thus preventing entrance of bacteria while the tributary tube 7 is not in use. During use of the tributary tube 7, the septum 10 may be punctured by a syringe needle for, for example, injecting an additional drug solution into the main drug solution. In case of the 3-way stopcock 1 as shown in FIGS. 12(a) and 12(b), the plug 50 is attached to the end of the tributary tube 7. The two components connected to one another have an increased length and, as a result, the volume of the drug solution that the tube can contain is increased by a corresponding amount. This increase in the volume of the flow passage of infusion fluid leads to formation of a dead space in which a small amount of the high concentration drug solution remains. As a result, dosage of the drug solution may fall short, or the drug solution may be wasted. Furthermore, if administration of an additional drug solution follows, the residual solution may be added to the additional solution, which results in an excessive dosage or a mixture of the added drug solution and the residual solution being administered to patients.

In general, when it is desired to collect blood samples during this type of infusion process, the infusion is interrupted to allow blood to flow back to upstream of the 3-way stopcock 1. Once the inrushing blood has filled adjacent area of the 3-way stopcock 1, the septum 10 of the 3-way stopcock 1 is punctured by a syringe needle to collect the undiluted blood. After collection of the blood samples, the infusion fluid is again allowed to flow in the positive direction through the flow passage of infusion fluid to push out the blood toward the blood vessel and clean the flow passage of infusion fluid.

However, the dead space as shown in FIGS. 12(a) and 12(b) impedes collection of blood samples through the septum 10 of the 3-way stopcock 1 using a syringe. This is a particularly serious problem in the case of arterial infusion, in which blood collection is essential. Further, the increased passage length increases generation of air bubbles 40 and makes it considerably difficult to remove the bubbles. In addition, such a dead space makes the deaeration process difficult during the brimming process when the infusion passage is filled with infusion fluid in the first place.

Furthermore, the large dead space can provide an ideal breeding ground for bacteria that enter the tube by accident.

In comparison, the 3-way stopcock 1 as shown in FIGS. 13(a) and 13(b) has a short tributary tube 7 and mitigates the problems associated with the dead space as described in reference to FIGS. 11 and 12. In such a construction, however, when the syringe 20 or the connector 22 is connected for side injection or mixed infusion of a drug solution, the needle of the syringe or the connector 22 that punctures the septum 10 and projects into the T-shaped switching conduit 16 interrupts switching operation of the infusion passage. In order to permit switching of the flow passage of infusion fluid, the syringe or the connector 22 must be pulled out each time the flow passage is switched. As a result, not only the advantage of the 3-way stopcock that the infusion passage can be freely switched is lost, but each insertion/removal of the syringe 20 or the connector 22 also increases the likelihood of bacteria entrance. This is also the case with the 3-way stopcock as shown in FIG. 14.

SUMMARY OF THE INVENTION

The present invention has been devised to address the above-mentioned problems associated with the prior art. Accordingly, it is an objective of the present invention to provide a sealable access stopcock that facilitates switching of the flow passage of infusion fluid as well as removal of air bubbles, has good isolation property for preventing microbial contamination, and is easy to operate to introduce a drug solution into a blood vessel while preventing stagnation of the drug solution.

According to the present invention, there is provided a sealable access stopcock including: a valve body having a switching part formed in a valve shaft thereof for switching from one flow passage to another; and a main body having an internal chamber in which the valve shaft of the valve body is rotatably fitted, and a plurality of tributary tubes each having a lumen extending therethrough, the lumen opening on a side wall of the internal chamber; the valve body being rotated to selectively bring the lumens into communication with one another through the switching part and thereby switch flow of an infusion fluid from one flow passage to another. This sealable access stopcock being characterized in that a switching channel in the form of an arcuate groove is formed in the switching part of the valve shaft to extend along the circumferential surface thereof.

According to the present invention, there is also provided a sealable access stopcock including: a valve body having a switching part formed in a valve shaft thereof for switching from one flow passage to another and a knob; and a main body having an internal chamber in which the valve shaft of the valve body is rotatably fitted, and a plurality of tributary tubes each having a lumen extending therethrough, the lumen opening on a side wall of the internal chamber; the valve body being rotated through the knob to selectively bring the lumens into communication with one another through the switching part and thereby switch flow of an infusion fluid from one flow passage to another. This sealable access stopcock is characterized in that at least one of the plurality of tributary tubes is a short tube having a septum, and a switching channel in the form of an arcuate groove is formed in the switching part of the valve shaft to extend along the circumferential surface thereof.

According to the present invention, there is also provided a sealable access stopcock including: a valve body having a switching part formed in a valve shaft thereof for switching from one flow passage to another and a handle; and main body in the form of a bottomed cylinder having an internal chamber in which the valve shaft of the valve body is rotatably fitted, and three tributary tubes each having a lumen extending therethrough, the lumen opening on a side wall of the internal chamber; the valve body being rotated through the handle to alternately bring the lumens into communication with one another through the switching part and thereby switch flow of an infusion fluid from one flow passage to another. This sealable access stopcock being characterized in that the three tributary tubes are formed by connecting a short tube having a septum to an elongate tube at the center of the elongate tube so that the short tube forms an angle of about 90° with respect to the elongate tube, and a switching channel in the form of an arcuate groove is formed in the switching part of the valve shaft to extend along the circumferential surface thereof.

According to the present invention, there is also provided a sealable access stopcock in which a switching valve is formed in the remaining part of the switching part other than the switching channel. The switching valve consists of a core having a circular cross-section and an umbrella-shaped closure portion extending along the circumferential surface thereof.

According to the present invention, there is also provided a sealable access stopcock in which a slit is formed in the septum for allowing passage of a needle.

According to the present invention, there is also provided a sealable access stopcock in which limitation means is provided for limiting the range of rotation of the valve body.

According to the present invention, there is also provided a sealable access stopcock in which click means is provided for stopping rotation of the valve body in a discrete manner.

For example, the stopcock of the present invention is used in the following manner. First, the handle of the valve body is turned to close the lumen of the tributary tube that is connected to a patient. Using a double thread and a tapered portion, an infusion tube is then connected to each of the two tributary tubes that form a main conduit. The infusion tube that is upstream of the other is connected to a source of infusion fluid. The valve body is then turned through the handle to open the lumen of the tributary tube on the side of a discharge port. As the lumen of the discharge-side tributary tube is opened, the infusion fluid reaches an end of the infusion tube. The infusion tube filled with the infusion fluid to the end thereof is then connected to an indwelling needle placed in the blood vessel of the patient. Through the main conduit, a primary drug solution is introduced into the body of the patient (blood vessel) via the switching channel of the valve shaft. The infusion fluid flows through the main conduit Rm as it smoothly passes through the switching channel, which is formed as an arcuate groove. Upon mixed infusion or side injection, the flow of infusion fluid can be switched from one flow passage to another by rotating the valve body through the handle while a sharp needle or a blunt needle is placed through the septum.

The present invention not only prevents entry of bacteria into the infusion fluid during administration of the primary drug solution through the main conduit but also significantly facilitates processes including collection of blood samples and removal of air bubbles because of the reduced length of the flow passage. Also, the present invention allows the valve body to be rotated during mixed infusion or side injection to switch from one flow passage to another with the sharp needle or the blunt needle placed through the septum and remaining within the switching channel. Accordingly, a highly operable sealable access stopcock is achieved. Further, the present invention, which includes limitation means for limiting the range of rotation of the valve body as well as click means for stopping rotation of the valve body in a discrete manner, provides a safe, manageable sealable access stopcock.

The present invention achieves a sealable access stopcock that facilitates switching of the flow passage of infusion fluid as well as removal of air bubbles, has good isolation property for preventing microbial contamination, and is easy to operate to introduce a drug solution into a blood vessel while preventing stagnation of the drug solution.

DETAILED DESCRIPTION OF THE INVENTION

First Embodiment

FIGS. 1(a) and 1(b) are schematic diagrams showing construction of a first embodiment of the present invention, where FIG. 1(a) is a frontal view; and FIG. 1(b) is a cross-section thereof. FIG. 2 is a cross-section taken along the line X—X in FIG. 1(a). FIGS. 3(a)–3(e) are schematic diagrams showing construction of a valve body according to the first embodiment, where FIG. 3(a) is a top view; FIG. 3(b) is a plan view; FIG. 3(c) is a frontal view; FIG. 3(d) is a right-side view; and FIG. 3(e) is a cross-section taken along the line Y—Y in FIG. 3(a).

Figure 1:
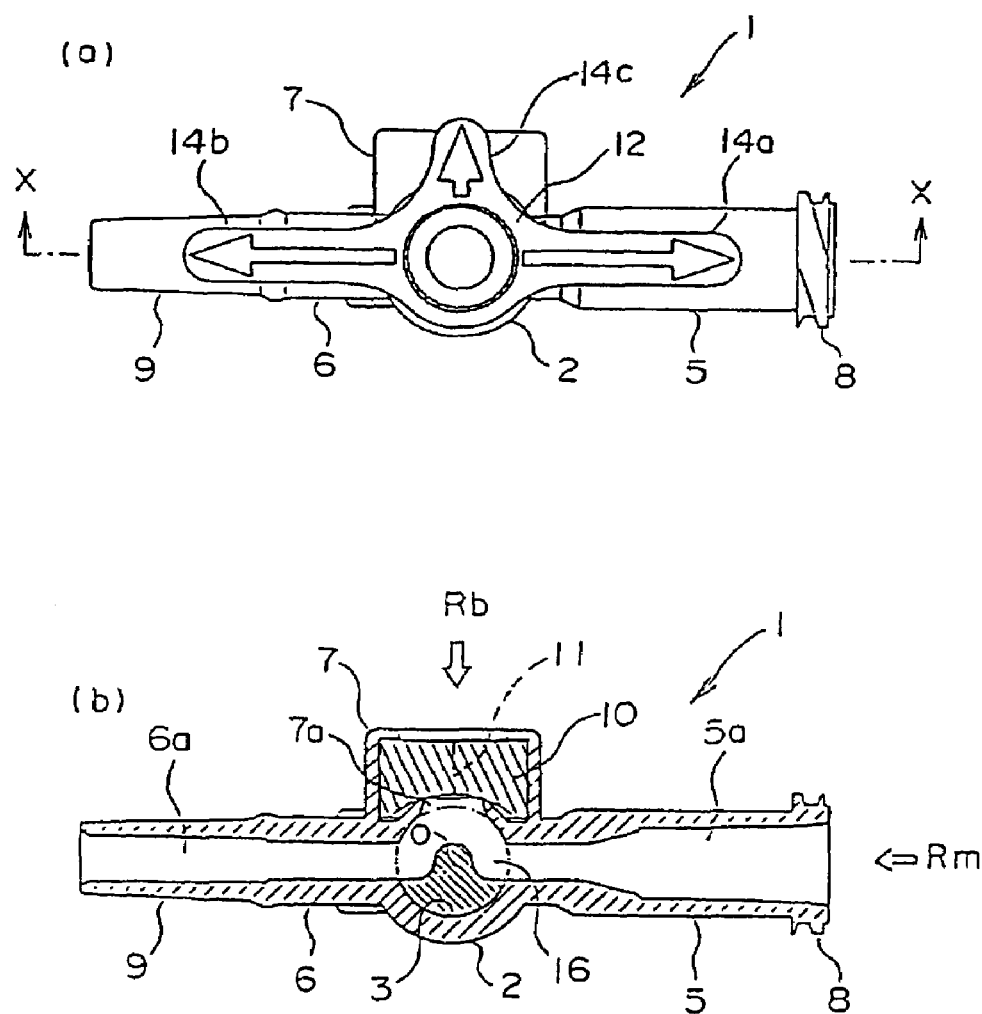
FIGS. 1(a) and 1(b) are schematic diagrams showing construction of first embodiment of the present invention.
Figure 2:
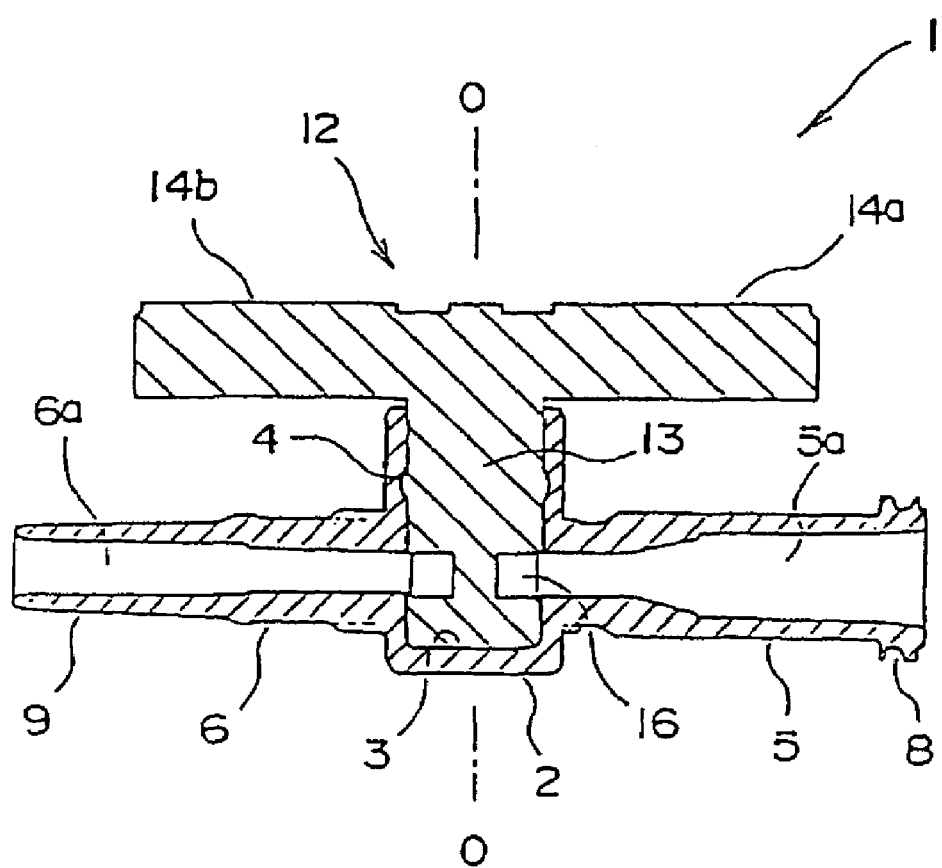
FIG. 2 is a cross-section taken along the line X—X in FIG. 1(a).
Figure 3:
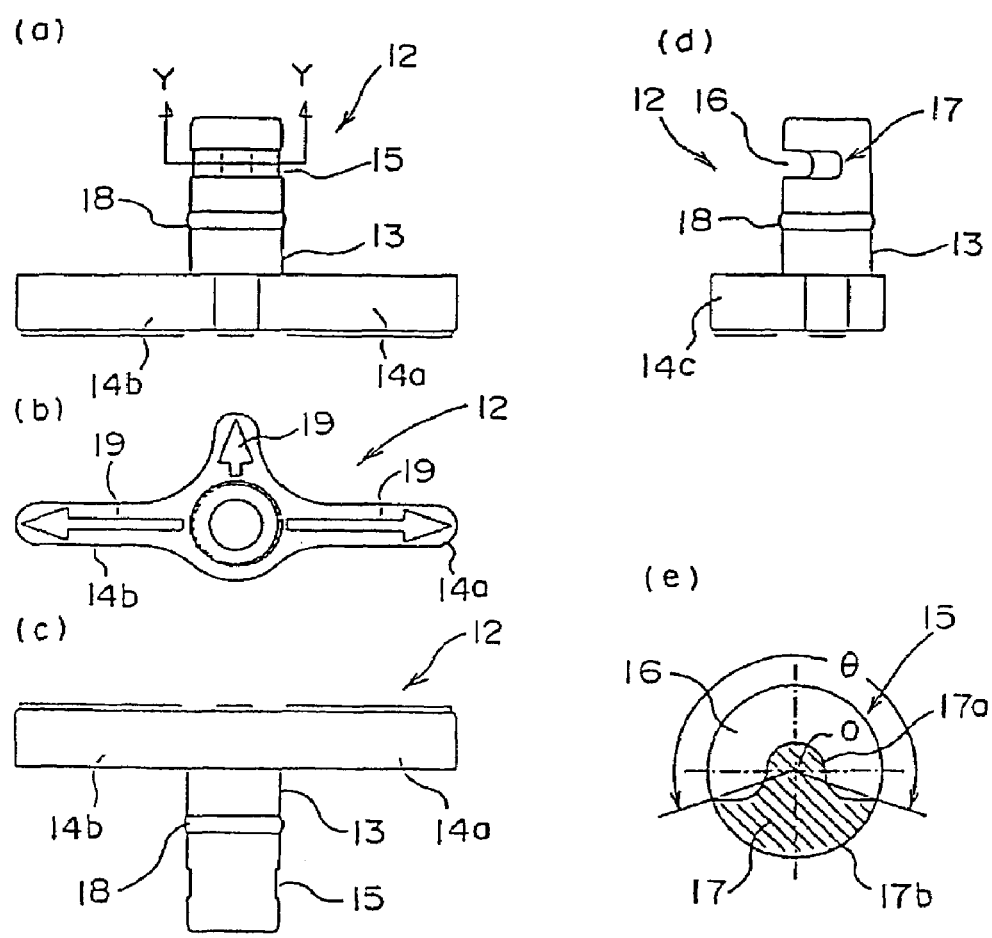
FIGS. 3(a)–3(e) are schematic diagrams showing construction of a valve body of the first embodiment.

Referring to FIGS. 1 and 2, a reference numeral 1 denotes a sealable access stopcock and a reference numeral 2 denotes a main body formed as a bottomed cylinder. The main body 2 is made of a transparent resin material such as polycarbonate (PC) and polyethylene terephthalate (PET) and PET/PC alloys. A reference numeral 3 denotes an internal chamber centered on a central axis O—O. A reference numeral 4 indicates an annular groove formed on the inner periphery of the internal chamber 3 along the circumferential direction.

Reference numerals 5, 6, and 7 denote tributary tubes that are separated from one another by an angle of about 90° and extend radially outward from the central axis O—O. Reference numerals 5a, 6a, and 7a are lumens of the respective tributary tubes, each of which opens into the internal chamber 3 of the main body 2. The tributary tubes 5 and 6 each have an elongate shape and are aligned with each other to form a main conduit Rm through which blood or a drug solution flows. The tributary tube 7 is much shorter than the tributary tubes 5 and 6, and forms a branch conduit Rb that intersects the main conduit Rm. Reference numerals 8 and 9 denote a double thread and a tapered portion for connection formed on ends of the tributary tubes 5 and 6, respectively, while a reference numeral 10 indicates a septum disposed in the tributary tube 7. Since the tributary tube 7 is very short, the inner space thereof is filled with the septum 10 as shown by the hatches in FIG. 1(b). The septum 10 is an elastic body formed from materials such as synthetic rubber and has a slit 11 through which a blunt or a sharp needle is passed upon addition of a drug solution in a side injection or a mixed injection process or collection of blood samples.

Reference numerals 12 and 13 denote a valve body and a valve shaft, respectively. The valve shaft 13 forms a cylindrical portion below the valve body 12. Reference numerals 14a and 14b denote handles, which are formed above the valve shaft 13 and extend horizontally in opposite directions. The valve body 12 and the main body 2 are integrated with each other and together form the sealable access stopcock 1. The valve body 12 is made of a plastic material such as polyethylene and polypropylene and, unlike the main body 2, is colored by an opaque color resin. A short projection 14c is formed to intersect the horizontally extending handles 14a and 14b such that the valve body 12 has a similar contour to the main body 2 when viewed in a plan view.

The structure of the valve body 12 is shown in its particularity in FIG. 3(a) through FIG. 3(e) in partial views. A reference numeral 15 denotes a switching part that forms a disk portion in the valve shaft 13 and faces the lumens 5a through 7a of the main body 2. The cross-section of the switching part 15 is shown in FIG. 3(e). As can also be seen from FIG. 1(b), FIGS. 4(b)–4(c) and FIG. 5, the switching part 15 is located right under the lumen 7a of the short tributary tube 7. A reference numeral 16 denotes a switching channel of the switching part 15 while a reference numeral 17 denotes a switching valve forming the remainder of the element. As shown, the switching channel 16 is formed as an arcuate groove extending along a circumferential surface so that the cross-section of the switching valve 17 consists of a circular core 17a and an umbrella-shaped closure portion 17b. The circular core 17a that is formed about the central axis O—O at a lower end of the switching valve 17 serves to make smooth the flow of infusion fluid and reinforce the switching part 15 of the valve shaft 13. The angle θ of the switching channel 16 substantially corresponds to the angle over which the lumens 5a through 7a are arranged.

A reference numeral 18 denotes a ridge 18 formed about the valve shaft 13 and corresponds to the groove 4. Reference numerals 19 denote arrow signs placed on the handles 14a and 14b and the projection 14c, respectively, with each sign directing each of the three directions. The arrow on the projection 14c is aligned with the central line of the switching channel 16. The valve shaft 13 is inserted into the internal chamber 3 from above and is placed therewithin in a rotatable, liquid-tight manner. With the valve shaft 13 placed in the internal chamber 3, the switching channel 16 and the switching valve 17 face the lumens 5a through 7a on the respective same radii. The valve shaft 13 is positioned in the internal chamber 3 by the ridge 18 engaging the groove 4. The engagement of the ridge 18 with the groove 4 prevents the valve shaft 13 from exiting from the internal chamber 3 and serves to maintain the liquid-tightness against the internal chamber 3. Thus, the valve body 12 can be turned through the handles 14a and 14b to open or close communication among the lumens 5a through 7a via the switching channel 16 so that the flow passage is switched between the main conduit Rm and the branch conduit Rb.

Next, the flow of a primary drug solution through the stopcock of the first embodiment having the construction described thus far is described with reference to the accompanying drawings.

Figure 4:
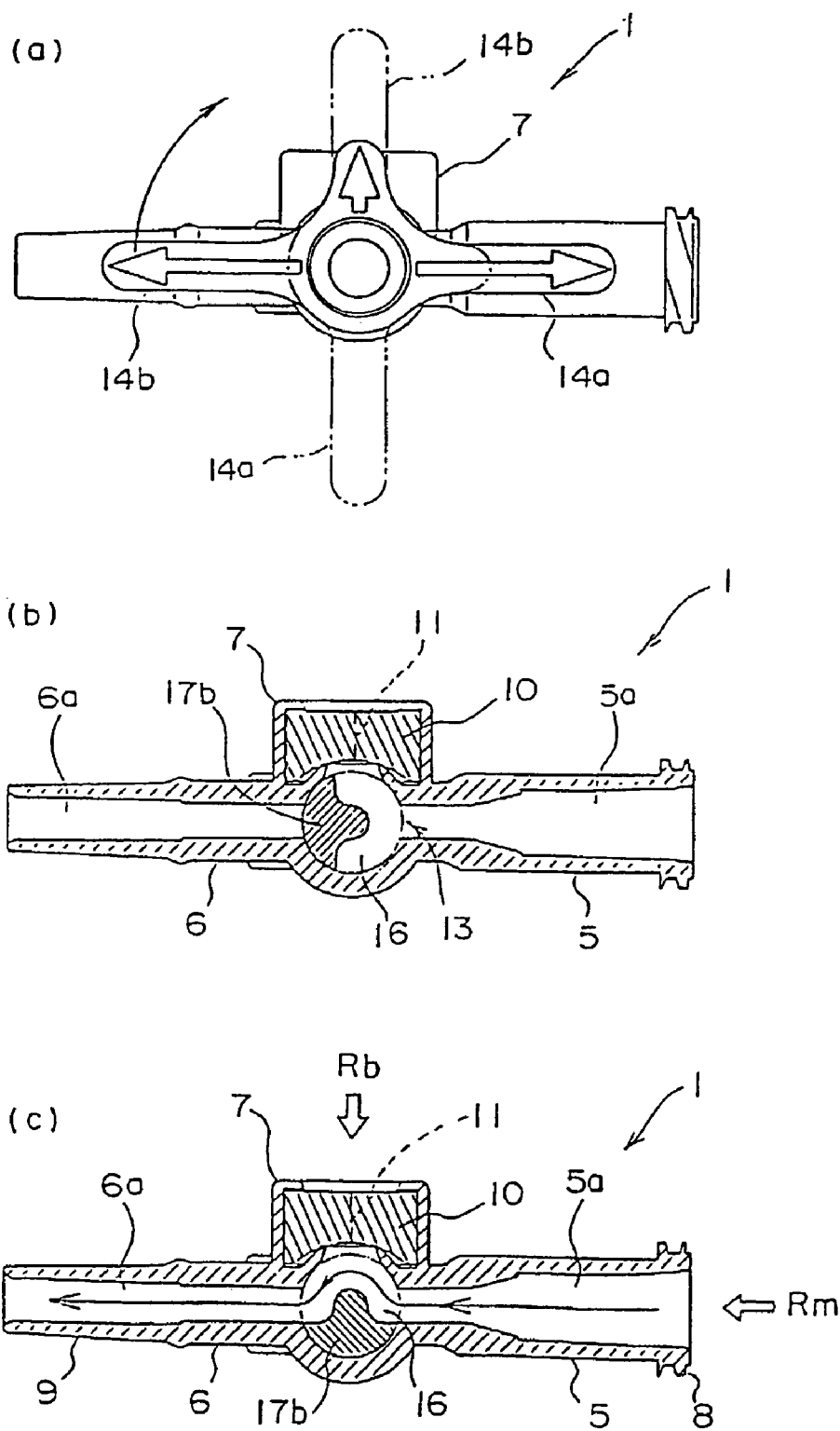
FIGS. 4(a)–4(c) are schematic diagrams showing an example of operation of the first embodiment.

First, the handles 14a and 14b are placed at a position as indicated by the double-dotted line in FIG. 4(a). When the handles 14a and 14b are in this position, the closure portion 17b of the switching valve 17 closes the opening of the lumen 6a in the internal chamber 3 as shown in FIG. 4(b). An infusion tube (not shown) is connected to each of the tributary tubes 5 and 6 by making use of the double thread 8 and the tapered portion 9. The infusion tube connected to the tributary tube 5 is connected on the other end to a source of infusion fluid such as an ampul. When the valve body 12 is rotated clockwise by 90° through the handles 14a and 14b from the position indicated by the double-dotted line to a position indicated by the solid line in FIG. 4(a), communication of the lumen 6a of the tributary tube 6 is established.

Figure 5:
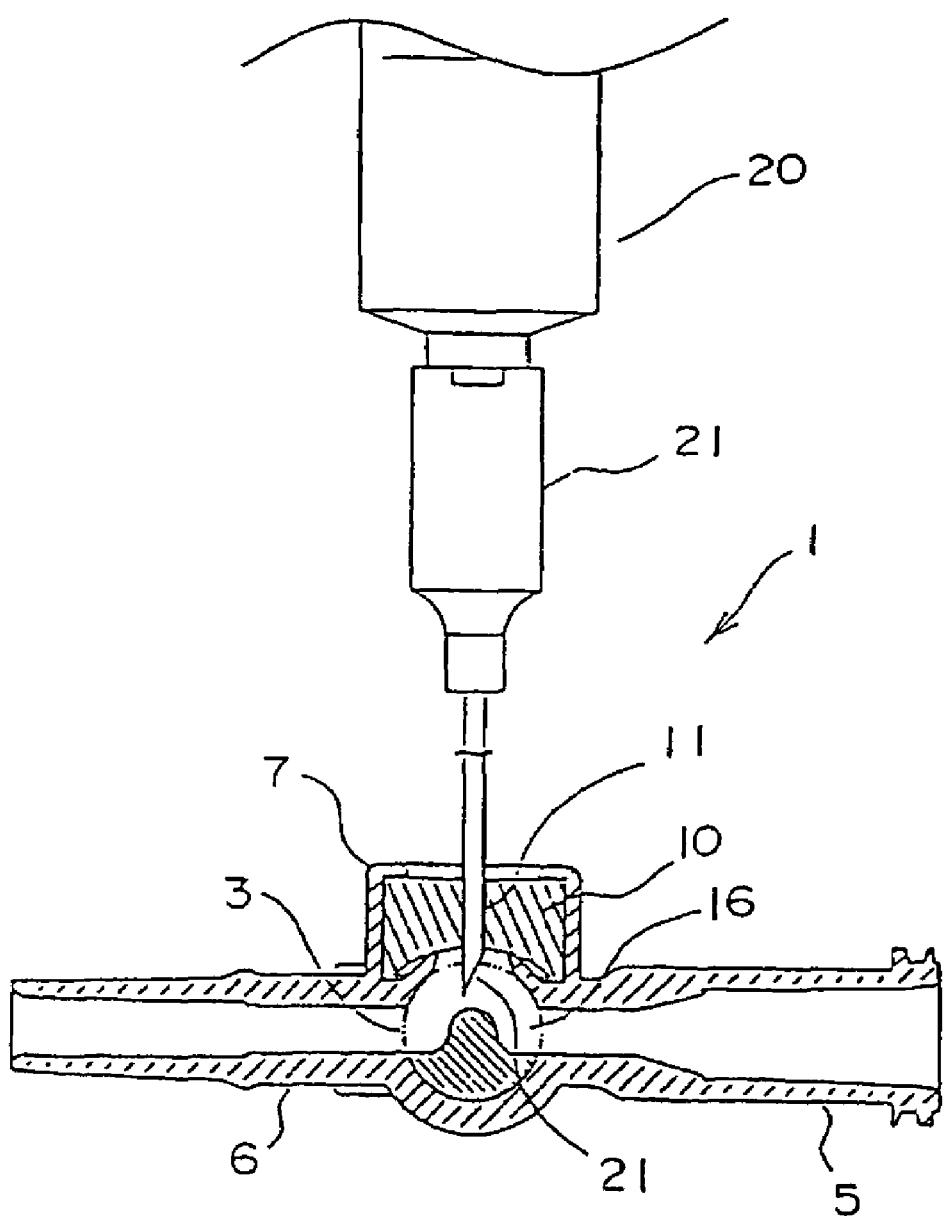
FIG. 5 is an explanatory view showing an advantageous aspect of the first embodiment.

When communication of the lumen 6a is opened, the infusion fluid flows through the infusion tube connected to the tributary tube 6 to an end thereof. The infusion tube filled with the infusion fluid to its end is connected to an indwelling needle placed in a blood vessel of a patient. A primary drug solution is infused into the body of the patient (blood vessel) through the main conduit Rm that connects the tributary tube 5 to the tributary tube 6 via the switching channel 16 of the valve shaft 13. The flow of the primary drug solution is indicated by an arrow in FIG. 4(c). As indicated by the arrow, the infusion fluid flows through the main conduit Rm as it smoothly passes through the arcuate switching channel 16. Since the inner space of the tributary tube 7 is filled with the septum 10 as noted above, the septum 10 isolates the inside of the sealable access stopcock 1 from the surrounding atmosphere during infusion and prevents entry of bacteria into the primary drug solution flowing through the main conduit Rm. Upon side injection of a small amount of a high concentration drug solution, the lumen 6a is also closed by the switching valve 17. In this state, a sharp needle 21 of a syringe is passed through the slit 11 of the septum 10 toward the central axis of the internal chamber 3. Once the needle is introduced, the handles 14a and 14b are rotated by 180° in the same manner as described above to open communication of the lumen 6a and thus form the branch conduit Rb as shown in FIG. 5 connecting the tributary tube 7 to the tributary tube 6 for injection. A plunger of the syringe 20 is then pushed thereinto to push out the small amount of the high concentration drug solution from the sharp needle 21 exposed in the switching channel 16. In this manner, the small amount of the high concentration drug solution is directly injected from the switching channel 16 into the tributary tube 6 in one shot. As a result, the side-injected solution flows through the arcuate switching channel 16 and is introduced into the blood vessel of the patient in a smooth and quick fashion. In this regard, because the tributary tube 7 is very short, no dead space is formed within the tributary tube 7. Subsequently, the handles 14a and 14b are returned to the position as shown in FIG. 4(b) to close the lumen 6a, and the sharp needle 21 is pulled out from the septum 10. This completes the side injection process.

Figure 6:
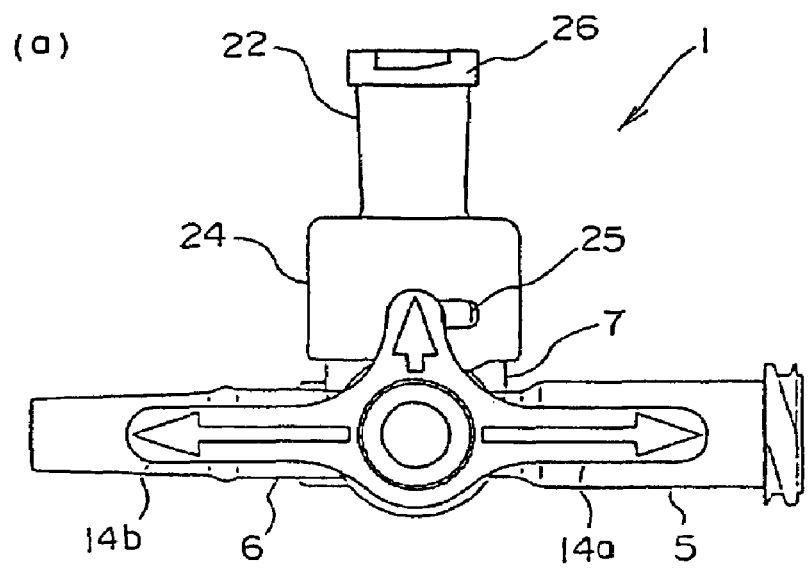
FIGS. 6(a) and 6(b) are schematic diagrams showing another advantageous aspect of the first embodiment.
Figure 6:
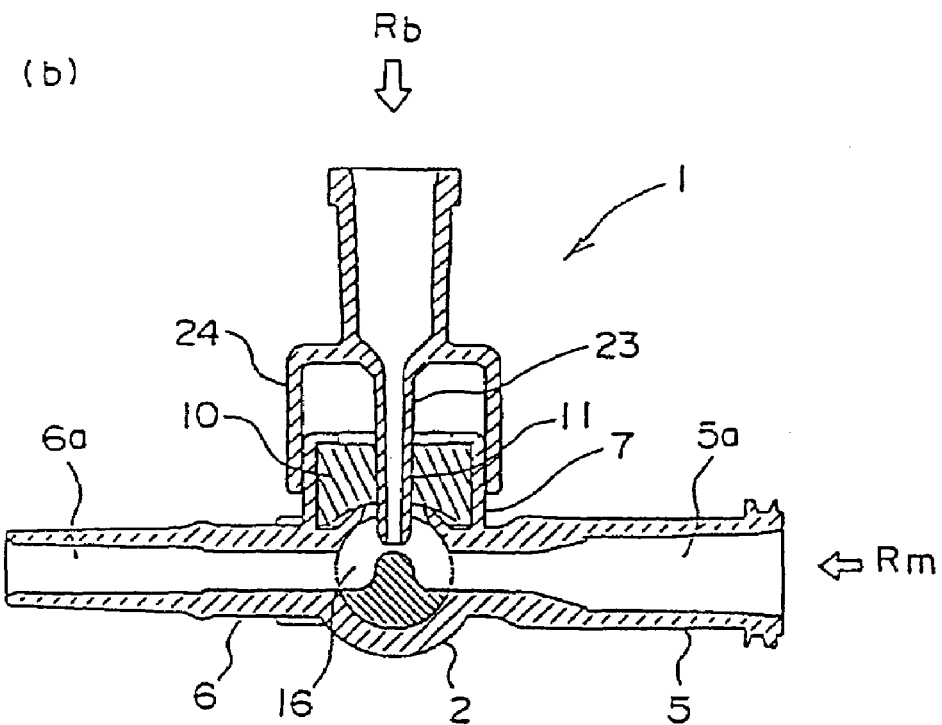
Figure 7:
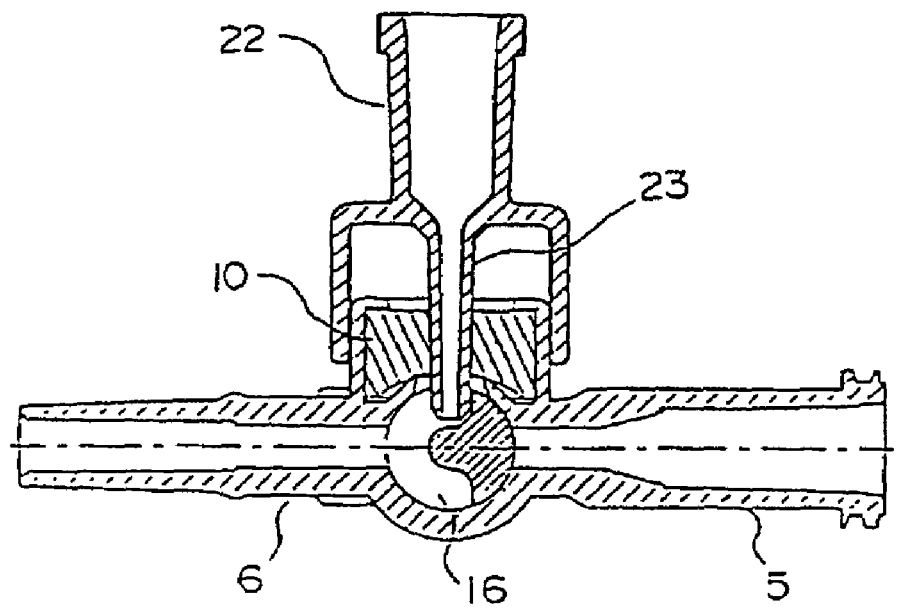
FIGS. 7(a) and 7(b) are schematic diagrams showing an example of switching operation of the first embodiment.
Figure 7:
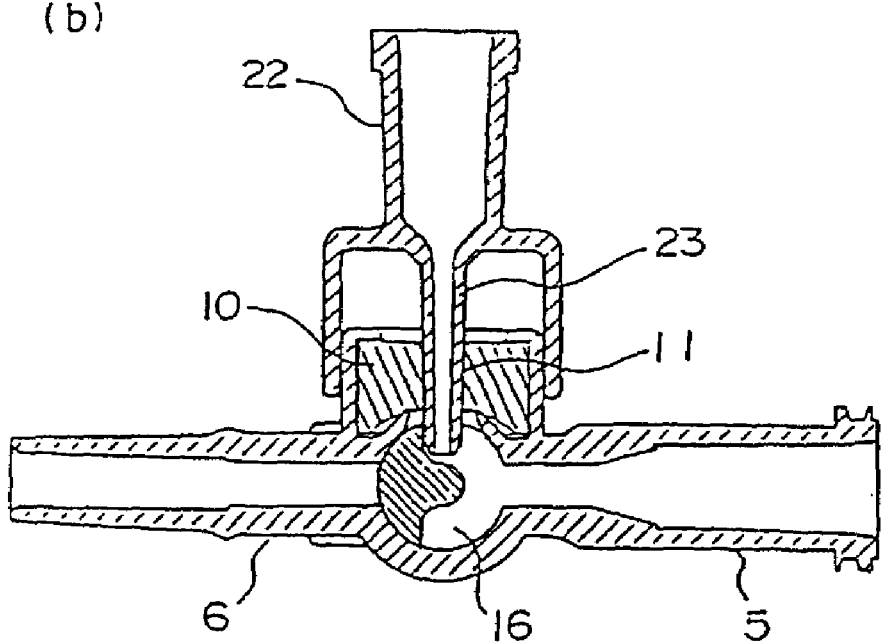

When it is desired to continuously introduce another drug solution during infusion of the primary drug solution, a connector 22 such as those shown in FIGS. 6 and 7 are used. Reference numerals 23, 24, 25, and 26 denote a blunt needle (or cannula) of the connector 22, a connector tube placed about the blunt needle 23, a connection slot, and a double thread, respectively. Though not specifically shown, the connection slot 25 is formed as a key-shaped slot, and an engage pin (not shown), which projects from the outer periphery of the tributary tube 7 at a position corresponding to the connection slot 25, is placed therethrough. By placing the connector tube 24 over the outer periphery of the tributary tube 7 with the engage pin engaging the connection slot 25 and slightly rotating the connector tube 24, the connector 22 is locked against the main body 2, providing removable connection thereto.

The lumen 6a is also closed when it is necessary to continuously introduce another drug solution for mixed infusion. The connector 22 is connected to the tributary tube 7 in the above-described manner as shown in FIGS. 6 and 7. Once the connector 22 is connected to the tributary tube 7, the blunt needle 23 is passed through the slit 11 of the septum 10. The handles 14a and 14b are then positioned parallel to the tributary tubes 5 and 6 to open the lumen 6a. As a result, the secondary solution, supplied through an infusion tube connected to the connector 22, is introduced through the blunt needle 23 into the primary solution flowing through the main conduit Rm and is mixed therewith in the switching channel 16. From the switching channel 16, the mixed solution flows through the lumen 6a of the tributary tube 6 and then the infusion tube and is continuously introduced into the body of the patient (blood vessel). The drug solution, as it is discharged from the blunt needle 23, is readily mixed into the primary solution within the switching channel 16 to be administered. Again, no dead space is formed within the tributary tube 7.

When it is desired to collect blood samples, the handles 14a and 14b are turned to close the lumen 6a and thus interrupt the mixed infusion through the blunt needle 23. A sharp needle 21 of a syringe is passed through the slit 11 of the septum 10 in the same manner as described in reference to FIG. 5. Blood is sucked through the tributary tube 6 and collected into the syringe 20 without being diluted with the infusion solution by pulling a plunger of the syringe 20. Once collection of blood samples is finished, infusion fluid is passed to push the blood back into the blood vessel and clean the flow passage. In this manner, blood samples can be collected by means of the sharp needle 21 directly inserted into the switching channel 16 of the valve shaft 13 without having the blood diluted with the infusion fluid since no dead space is formed within the tributary tube 7.

When air bubbles form in the flow passage of infusion fluid, a syringe, having air bubbles removed from its injection cylinder, is mounted with its needle piercing through the septum 10. Then, the plunger of the syringe 20 is pulled by the knob to suck the air bubbles into the sharp needle 21. In this manner, air bubbles present in the infusion fluid can be readily removed. Further, the smooth flow of the infusion fluid through the arcuate switching channel 16 substantially reduces air bubble generation, simplifying the deaeration process.

As set forth, the sealable access stopcock 1 according to the first embodiment includes the short tributary tube 7 having the septum 10 for isolating from the surrounding environment and serves to switch the flow of infusion fluid from one flow passage to another by means of the switching channel 16, which is formed as an arcuate groove extending along the circumferential surface of the valve shaft 13. Not only does this construction prevent entry of bacteria into the infusion fluid during administration of the primary drug solution through the main conduit Rm, but it also significantly facilitates processes including collection of blood samples and removal of air bubbles because of the reduced length of the flow passage. Also, this construction allows the handles 14a and 14b to be turned during mixed infusion or side injection to switch from one flow passage to another with the sharp needle 21 or the blunt needle 23 placed through the septum 10 and remaining within the switching channel 16. Accordingly, a highly operable sealable access stopcock 1 can be provided.

Second Embodiment

Figure 8:
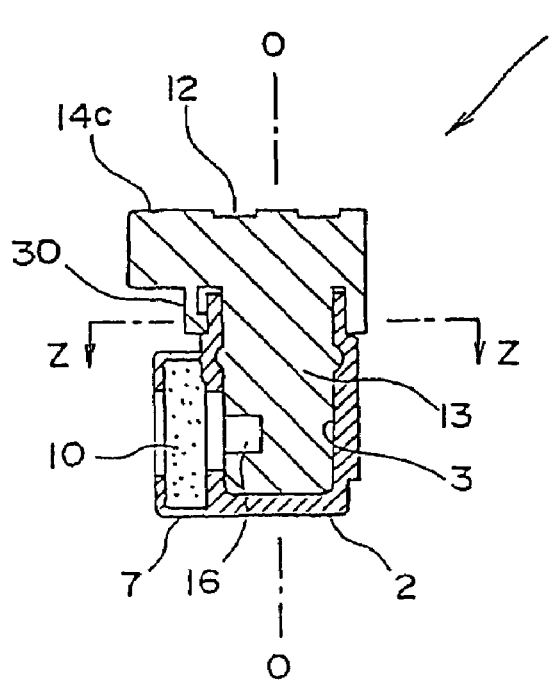
FIG. 8 is a cross-section showing major components of a second embodiment of the present invention.
Figure 9:
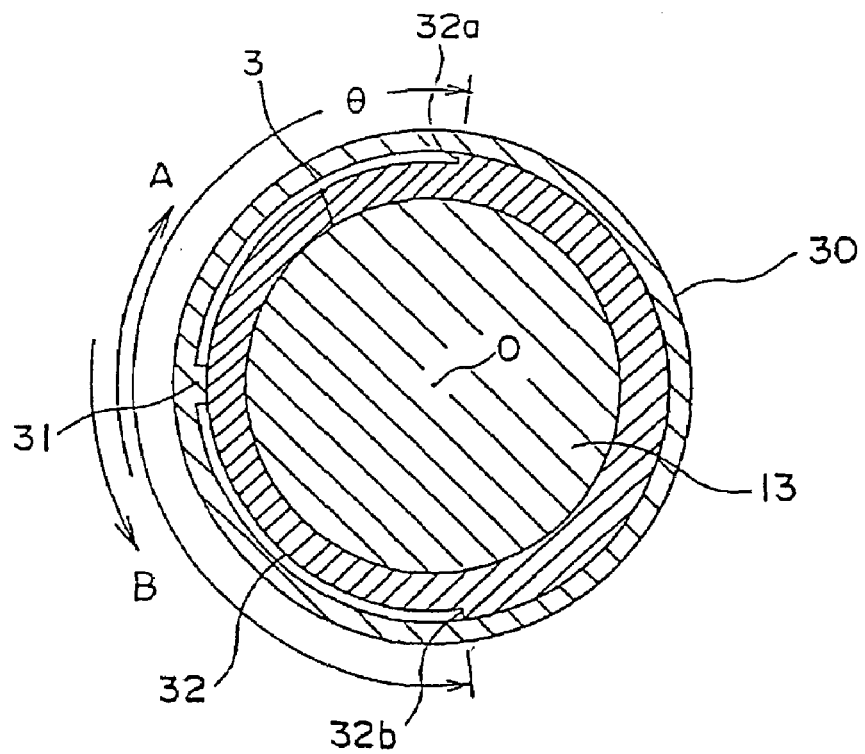
FIG. 9 is an enlarged cross-section taken along the line Z—Z in FIG. 8.

FIG. 8 is a cross-section of one construction of a second embodiment of the present invention showing major components thereof while FIG. 9 is an enlarged cross-section taken along the line Z—Z in FIG. 8.

In FIGS. 8 and 9, a reference numeral 30 denotes a limitation tube placed about the valve shaft 13 of the valve body 12, a reference numeral 31 denotes a limitation projection projecting from the inner surface of the limitation tube, and a reference numeral 32 denotes an arcuate cutout formed along the outer periphery of the main body 2 at the top end thereof. The angle of the cutout 32 formed on the main body 2 is substantially the same as the above-described angle θ of the arch of the switching channel 16. The limitation projection 31 on the valve body 12 engages the cutout 32.

When the valve body 12 is turned through the handles 14a and 14b to switch from one flow passage to another, the limitation projection 31 slides within the arcuate cutout 32. The valve body 12 can be rotated through the handles 14a and 14b in the direction indicated by an arrow A until the limitation projection 31 comes into contact with a left limit 32a of the cutout 32 whereas it can be rotated in the direction B until the limitation projection 31 comes into contact with a right limit 32b. In other words, rotation of the valve shaft 13 is limited within the range of angle θ. This construction prevents the sharp needle 21 or the blunt needle 23 projecting in the switching channel 16 from bending or breaking. In this manner, rotation over the angle θ can easily be limited since part of the limitation tube 30, which has a larger diameter than the valve shaft 13, serves to limit the rotation.

Third Embodiment

Figure 10:
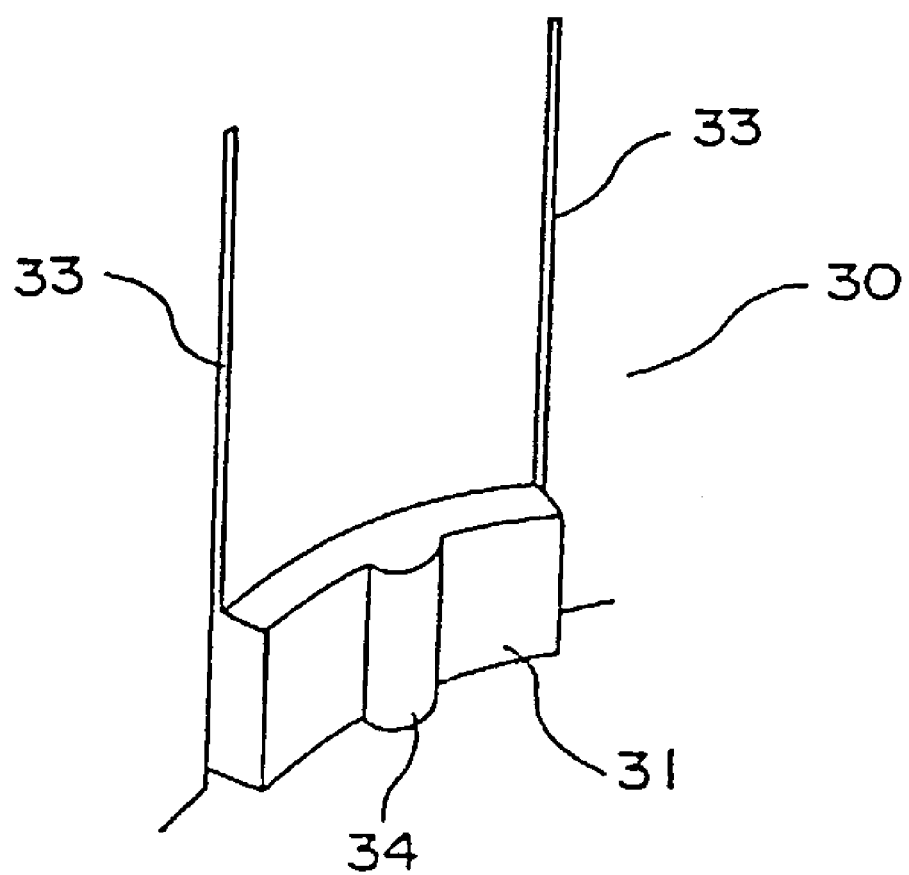
FIG. 10 is an enlarged perspective view showing major components of a third embodiment.
Figure 11:
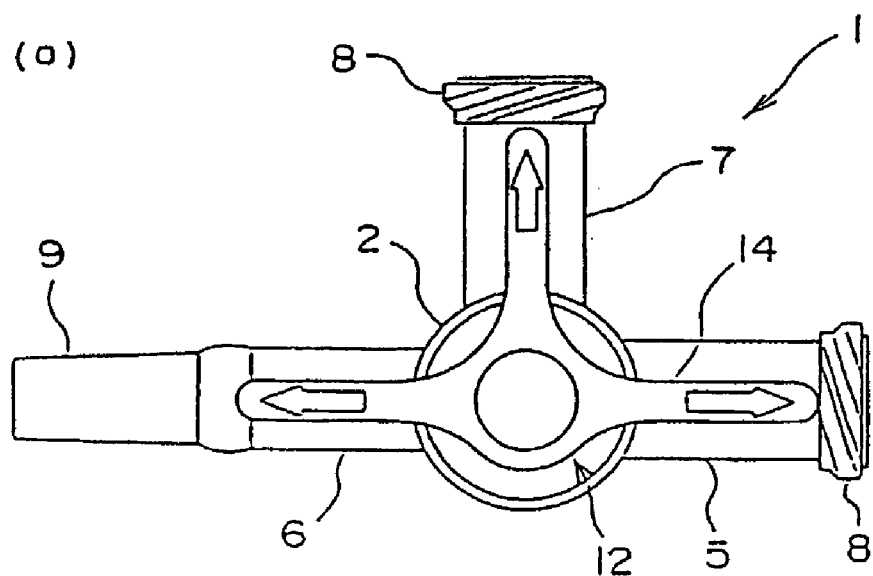
FIGS. 11(a) and 11(b) are schematic diagrams showing construction of a conventional 3-way stopcock.
Figure 11:
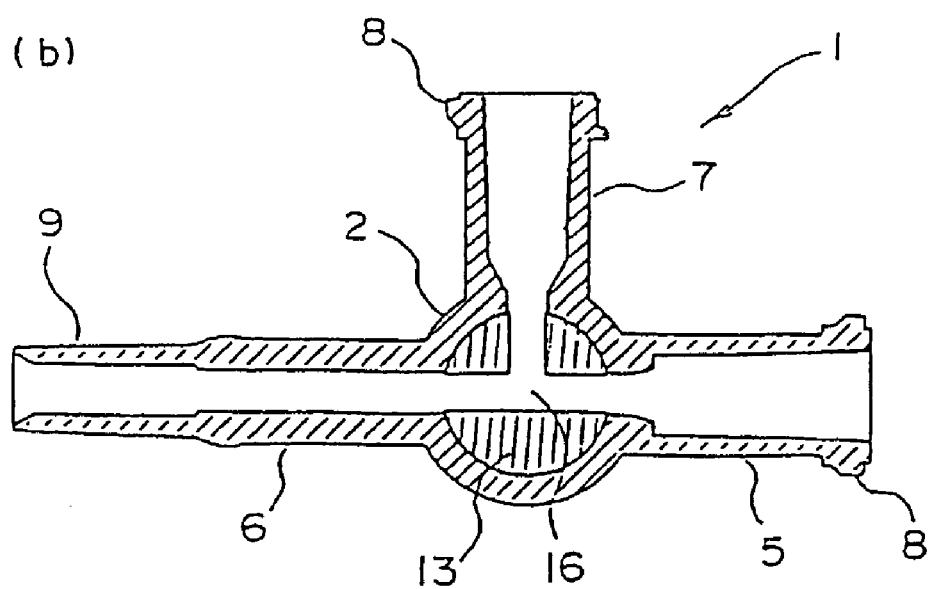
Figure 12:
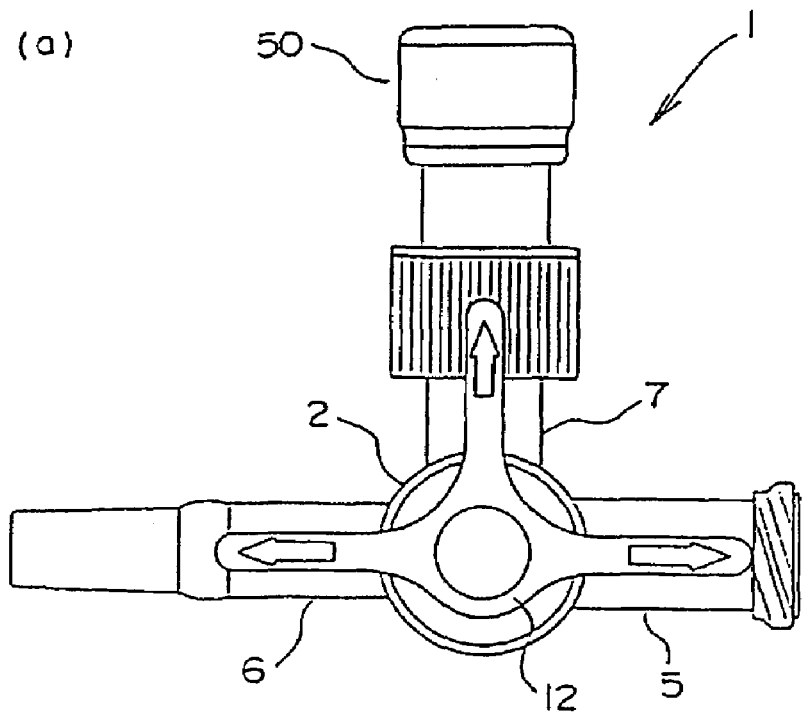
FIGS. 12(a) and 12(b) are schematic diagrams showing one application of the conventional 3-way stopcock.
Figure 12:
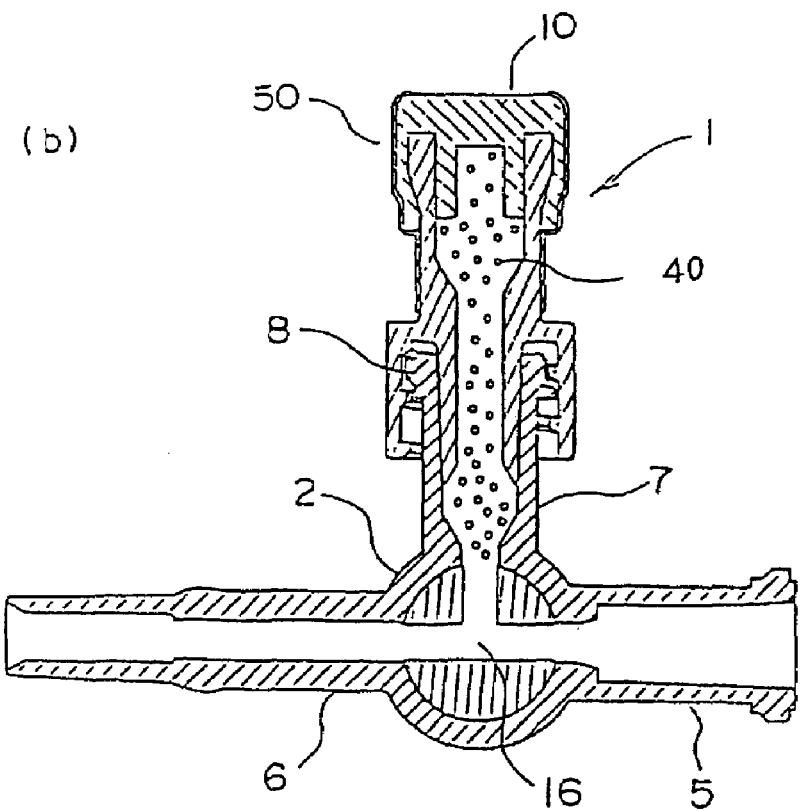
Figure 13:
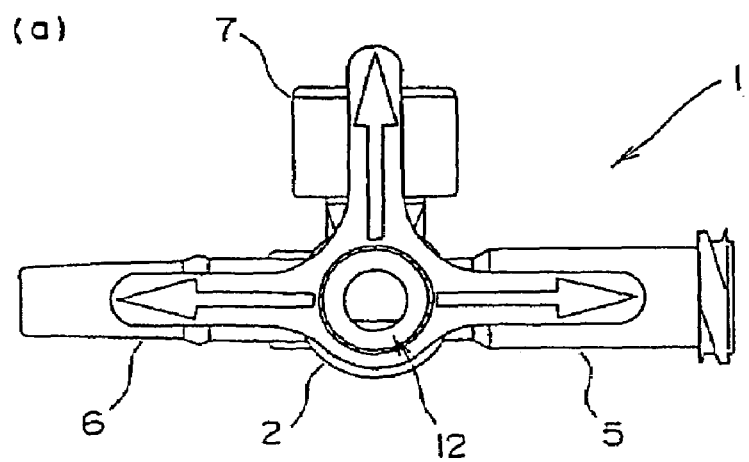
FIGS. 13(a) and 13(b) are schematic diagrams showing another application of the conventional 3-way stopcock.
Figure 13:
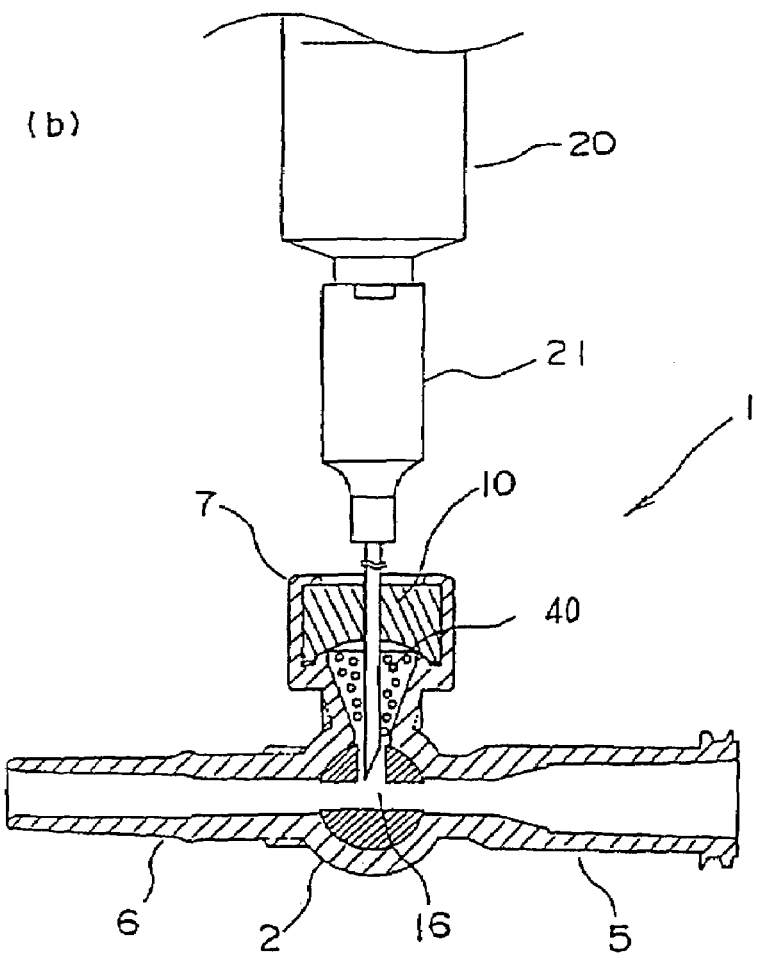
Figure 14:
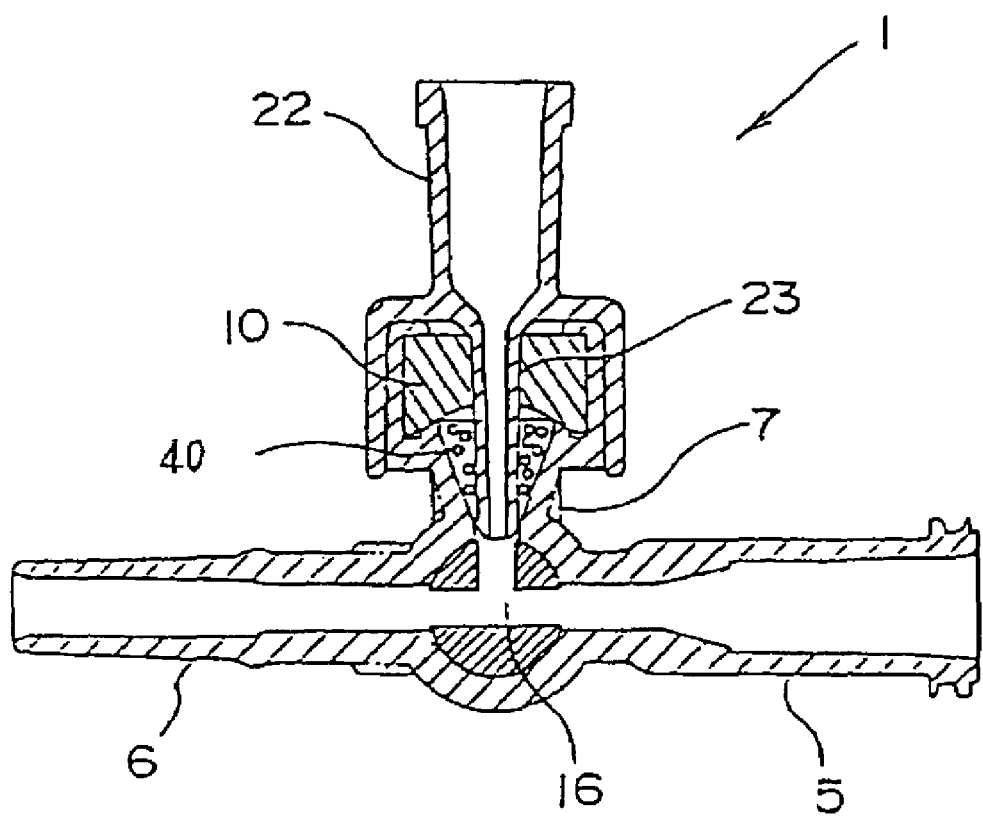
FIG. 14 is an explanatory view showing one application of the construction shown in FIG. 13.

Referring to FIG. 10, major components of a third embodiment are shown in an enlarged perspective view. This embodiment employs a construction featuring a click function for causing the valve shaft to snap into position at different positions, in addition to the above-described function of the second embodiment for limiting the rotation angle.

In FIG. 10, a reference numeral 33 denotes a slit formed on either side of the limitation projection 31, which was described in the second embodiment above. A reference numeral 34 denotes a semicircular protrusion. The slits 33 allow the limitation projection 31 to resiliently move in the radial direction with respect to the central axis O—O. Accordingly, the protrusion 34 can be resiliently displaced in the radial direction.

Though not shown, the cutout 32 of the main body 2 shown in FIG. 9 includes three axial grooves each having a semicircular cross-section that corresponds to the protrusion 34. The grooves are formed at three different positions. As the valve body 12 is rotated through the handles 14a and 14b, the protrusion 34 snaps into each of the semicircular grooves and is stopped in a discrete manner. The three discrete click positions at which the protrusion 34 comes to stop correspond to respective positions of the closure portion 17b of the switching valve 17 for closing the lumens 5a, 6a, and 7a.

The third embodiment is advantageous in that it can provide a sealable access stopcock 1 that features two functions of limiting rotation of the valve body 12 and stopping the valve body 12 in a discrete manner.

While in the above-described embodiment, the three tributary tubes to form the main conduit are separated from one another by 90°, the three tributary tubes may be spaced apart by equal or unequal distances and are arranged within 180° range. Also, a greater or fewer number of the tributary tubes may be provided. Further, while in the example shown, two handles are provided on both sides of the valve shaft, a conventional construction or a cantilever-type construction may also be employed, or in some cases, a dial-shaped knob may be employed. Also, while the valve shaft has a cylindrical shape with a uniform diameter, it may have a multi-step construction. Constructions other than those described in reference to the above embodiments may also be contemplated in terms of shapes of the main body or other aspects of the present invention.

The invention claimed is:

1. A cock for medical use, comprising:
   a valve body having a switching part formed in a valve shaft thereof for switching from one flow passage to another by operation of a handle; and
   a main body in the form of a bottomed cylinder having an internal chamber in which the valve shaft of the valve body is rotatably fitted, and three tributary tubes each having a lumen extending therethrough, the lumen opening on a side wall of the internal chamber;
   the valve body being rotated through the handle to alternately bring the lumens into communication with one another through the switching part and thereby switch flow of an infusion fluid from one flow passage to another;
   wherein one of the tributary tubes is a patient side tributary tube for connection to the patient and other two tributary tubes are source side tributary tubes for connection to infusion sources;
   wherein one of the source side tributary tubes is made much shorter than the other source side tributary tube and the patient side tributary tube; and wherein the long source side tributary tube is arranged in line with the patient side tributary tube;
   wherein the short source side tributary tube is arranged at an angle of about 90° with respect to the other tributary tubes, and the short source side tributary tube is filled with a septum so as to substantially eliminate dead space in the tributary tube; and
   wherein the switching part is located right under the lumen of the short source side tributary tube, and wherein the switching part comprises a switching valve which has a cross section consisting of a semicircular closure portion along the circumferential surface of the valve shaft and a semicircular core portion with a smaller radius than the semicircular closure portion so as to form a switching channel in a form of an arcuate groove in the valve shaft.

2. The cock for medical use according to claim 1, wherein a slit is formed in the septum for allowing passage of a needle.

3. The cock for medical use according to claim 1, wherein limitation means is provided for limiting the range of rotation of the valve body.

4. The cock for medical use according to claim 1, wherein click means is provided for stopping rotation of the valve body in a discrete manner.

5. The cock for medical use according to claim 1, wherein the switching channel is so formed that the valve body can be rotated even when a needle of a syringe or a connector is exposed in the switching channel.

* * * * *